United States Patent
Klimek et al.

(10) Patent No.: US 11,944,454 B2
(45) Date of Patent: Apr. 2, 2024

(54) TISSUE INTERFACE (71) Applicant: Nonin Medical, Inc., Plymouth, MN (US)

(72) Inventors: Scott Gregory Klimek, Maple Grove, MN (US); Gregory J. Rausch, Minnetonka, MN (US)

(73) Assignee: NONIN MEDICAL, INC., Plymouth, MN (US)

( * ) Notice: Subject to any disclaimer, the term of this patent is extended or adjusted under 35 U.S.C. 154(b) by 922 days.

(21) Appl. No.: 15/503,943

(22) PCT Filed: Aug. 14, 2015

(86) PCT No.: PCT/US2015/045306
§ 371 (c)(1),
(2) Date: Feb. 14, 2017

(87) PCT Pub. No.: WO2016/025851
PCT Pub. Date: Feb. 18, 2016

(65) Prior Publication Data
US 2017/0231566 A1    Aug. 17, 2017

Related U.S. Application Data

(60) Provisional application No. 62/057,065, filed on Sep. 29, 2014, provisional application No. 62/037,948, filed on Aug. 15, 2014.

(51) Int. Cl.
*A61B 5/00* (2006.01)
*A61B 5/0205* (2006.01)
(Continued)

(52) U.S. Cl.
CPC .......... *A61B 5/6804* (2013.01); *A61B 5/0205* (2013.01); *A61B 5/02055* (2013.01);
(Continued)

(58) Field of Classification Search
CPC . A61B 5/6804; A61B 5/0205; A61B 5/02055; A61B 5/14551; A61B 5/6802;
(Continued)

(56) References Cited

U.S. PATENT DOCUMENTS 4,947,853 A * 8/1990 Hon .................... A61B 5/6843
600/459
4,947,865 A    8/1990 Hon et al.
(Continued)

FOREIGN PATENT DOCUMENTS

EP    1752085    2/2007
EP    2505090    10/2012
(Continued)

OTHER PUBLICATIONS

"European Application Serial No. 15831631.5, Supplemental Partial European Search Report dated Mar. 5, 2018", 14 pgs.
(Continued)

*Primary Examiner* — Eric F Winakur
*Assistant Examiner* — Abid A Mustansir
(74) *Attorney, Agent, or Firm* — SCHWEGMAN LUNDBERG & WOESSNER P.A.

(57) ABSTRACT

A system includes a garment and a sensor module. The garment includes an engagement feature. The garment is configured to encompass a first location on a body. The engagement feature is positioned in fixed alignment with the garment. The sensor module includes a sensor housing and includes a sensor having an electrical node. The sensor is configured to provide an electrical output on the node. The housing has a complementary feature. The complementary feature is configured to couple and decouple with the engagement feature. The electrical output is based on a
(Continued)

measure of a physiological parameter associated with the body and is based on site information corresponding to the engagement feature.

17 Claims, 9 Drawing Sheets

(51) Int. Cl.
*A61B 5/024* (2006.01)
*A61B 5/145* (2006.01)
*A61B 5/1455* (2006.01)

(52) U.S. Cl.
CPC ........ *A61B 5/14551* (2013.01); *A61B 5/6802* (2013.01); *A61B 5/6843* (2013.01); *A61B 5/02416* (2013.01); *A61B 5/14535* (2013.01); *A61B 5/6831* (2013.01); *A61B 5/6832* (2013.01); *A61B 5/6838* (2013.01); *A61B 2562/225* (2013.01)

(58) Field of Classification Search
CPC .............. A61B 5/6843; A61B 5/02416; A61B 5/14535; A61B 5/6831; A61B 5/6832; A61B 5/6838; A61B 2562/225
See application file for complete search history.

(56) References Cited

U.S. PATENT DOCUMENTS

| | | | |
|---|---|---|---|
| 6,972,605 B1* | 12/2005 | Choe .................. | H03K 19/0963 327/199 |
| 8,190,229 B2 | 5/2012 | Lowery et al. | |
| 9,439,599 B2 | 9/2016 | Thompson et al. | |
| 9,668,682 B2 | 6/2017 | Brister et al. | |
| 9,839,384 B2 | 12/2017 | Escutia et al. | |
| 2002/0165462 A1* | 11/2002 | Westbrook ......... | A61B 5/14552 600/529 |
| 2003/0088385 A1 | 5/2003 | David | |
| 2004/0122302 A1 | 6/2004 | Mason et al. | |
| 2006/0258939 A1 | 11/2006 | Pesach et al. | |
| 2007/0036723 A1 | 2/2007 | Hayter | |
| 2007/0073125 A1* | 3/2007 | Hoarau ................ | A61B 5/6826 600/323 |
| 2007/0123763 A1* | 5/2007 | Al-Ali .................. | A61B 5/1455 600/344 |
| 2009/0076364 A1* | 3/2009 | Libbus ................ | A61B 5/0205 600/391 |
| 2010/0087717 A1 | 4/2010 | Onoe et al. | |
| 2011/0092790 A1 | 4/2011 | Wilder-Smith et al. | |
| 2012/0165645 A1 | 6/2012 | Russell et al. | |
| 2013/0085356 A1 | 4/2013 | Schlottau et al. | |
| 2013/0172724 A1* | 7/2013 | Ali Mohamed Aziz ..................... | A61N 1/0496 600/391 |
| 2013/0231046 A1 | 9/2013 | Pope et al. | |
| 2014/0156196 A1* | 6/2014 | Martinez .............. | A61B 5/0205 702/19 |
| 2014/0206976 A1 | 7/2014 | Thompson et al. | |
| 2014/0228649 A1 | 8/2014 | Rayner et al. | |
| 2015/0164422 A1* | 6/2015 | Lee ...................... | A61B 5/6831 600/300 |
| 2016/0038053 A1* | 2/2016 | Bohorquez .......... | A61B 5/0537 600/393 |

FOREIGN PATENT DOCUMENTS

| | | |
|---|---|---|
| JP | H04501224 | 3/1992 |
| JP | 2003102692 A | 4/2003 |
| JP | 2006527059 | 11/2006 |
| JP | 2007044510 | 2/2007 |
| JP | 2009509663 | 3/2009 |
| JP | 2009509672 | 3/2009 |
| JP | 2009519075 A | 5/2009 |
| JP | 2010538745 | 12/2010 |
| JP | 2014506504 A | 3/2014 |
| JP | 2014514032 | 6/2014 |
| WO | 2014066752 | 5/2014 |
| WO | WO-2016025851 A1 | 2/2016 |

OTHER PUBLICATIONS

Japanese Application Serial No. 2017-508027, Notification of Reasons for Refusal dated Feb. 25, 2020, w/ English Translation, 11 pgs.
Japanese Application Serial No. 2017-508027, Response filed Dec. 16, 2019 to Notification of Reasons for Refusal dated Jul. 16, 2019, w/ English Claims, 10 pgs.
"International Application Serial No. PCT/US2015/045306, International Search Report dated Dec. 23, 2015", 4 pgs.
"International Application Serial No. PCT/US2015/045306, Invitation to Pay Add'l Fees and Partial Search Report dated Oct. 1, 2015", 2 pgs.
"International Application Serial No. PCT/US2015/045306, Written Opinion dated Dec. 23, 2015", 9 pgs.
"European Application Serial No. 15831631.5, Extended European Search Report dated Jun. 25, 2018", 13 pgs.
"European Application Serial No. 15831631.5, Resposne filed Jan. 22, 2019 to Extended European Search Report dated Jun. 25, 2018", 17 pgs.
"Japanese Application Serial No. 2017-508027, Notification of Reasons for Refusal dated Jul. 16, 2019", w English translation, 12 pgs.
"European Application Serial No. 15831631.5, Response filed Oct. 2, 2017 to Communication pursuant to Rules 161(2) and 162 EPC dated Mar. 22, 2017", 12 pgs.
"International Application Serial No. PCT/US2015/045306, International Preliminary Report on Patentability dated Mar. 2, 2017", 8 pgs.
"European Application Serial No. 15831631.5, Communication pursuant to Rules 161(2) and 162 EPC dated Mar. 22, 2017", 2 pgs.
Japanese Application Serial No. 2017-508027, Final Notification of Reasons for Refusal dated Oct. 27, 2020, w/ English translation, 11 pgs.
Japanese Application Serial No. 2017-508027, Response filed Aug. 21, 2020 to Notification of Reasons for Refusal dated Feb. 25, 2020, w/ English Claims, 10 pgs.
"European Application Serial No. 21152482.2, Extended European Search Report dated May 17, 2021", 13 pgs.
"Japanese Application Serial No. 2017-508027, Response filed Apr. 26, 2021 to Final Notification of Reasons for Refusal dated Oct. 27, 2020", w/ English Translation, 15 pgs.
"Japanese Application Serial No. 2017-508027, Decision of Refusal dated Aug. 3, 2021", w/ English Translation, 8 pgs.
European Application Serial No. 21152482.2, Response filed Dec. 14, 2021 to Extended European Search Report, dated May 17, 2021, 9 pgs.
Canadian Application Serial No. 2,958,227, Examiner's Rule 86(2) Requisition dated Oct. 12, 2022, 4 pgs.
Canadian Application Serial No. 2,958,227, Response filed Mar. 10, 2022 to Office Action dated Sep. 16, 2021, 12 pgs.
Canadian Application Serial No. 2,958,227, Examiners Rule 86(2) Report dated Sep. 5, 2023, 4 pgs.
European Application Serial No. 21152482.2, Communication Pursuant to Article 94(3) EPC dated Jan. 22, 2024, 5 pgs.

* cited by examiner

TISSUE INTERFACE

This application is a U.S. National Stage Filing under 35 U.S.C. 371 from International Application No. PCT/US2015/045306, filed on Aug. 14, 2015, and published as WO 2016/025851 on Feb. 18, 2016, which claims the benefit of priority of U.S. Provisional Patent Application Ser. No. 62/037,948, filed on Aug. 15, 2014 and this application claims the benefit of priority of U.S. Provisional Patent Application Ser. No. 62/057,065, filed on Sep. 29, 2014, which applications and publication are herein incorporated by reference in their entirety.

CLAIM OF PRIORITY

This application claims the benefit of priority of U.S. Provisional Patent Application Ser. No. 62/037,948, filed on Aug. 15, 2014 and this application claims the benefit of priority of U.S. Provisional Patent Application Ser. No. 62/057,065, filed on Sep. 29, 2014, 2014, both of which are herein incorporated by reference in their entirety.

BACKGROUND

Sensors, such as physiological sensors are used to measure biological parameters associated with a patient. Many sensors are affixed to a patient with adhesive or with straps included on the sensor. Accordingly, such sensors do not have the capability to be reattached at a previous location of attachment. Many sensors include a wired connection to a power source or signal collection device.

In some examples, sensors are affixed to a patient with adhesive that can cause pain or injury to a patient during removal of the sensor. Some means of affixing a sensor can be permanent or leave a portion of the sensor apparatus on the patient.

OVERVIEW

The present inventors have recognized, among other things, that a problem of releasably attaching a sensor to a body of a patient can be solved by including an engagement feature in a garment worn by a patient. The engagement feature enables coupling and decoupling from a complementary feature included in a sensor module. Any combination of an engagement feature and a complementary feature can be provided on disposable device or on a non-disposable device.

For instance, a garment, such as a shirt, armband, headband, or the like can include an engagement feature. The engagement feature can include, but is not limited to, a snap, pin, magnet, hook and loop fastener, zipper, press-fit, snap-fit, quick release fastener, or the like. A sensor module including a sensor, sensor housing, and electrical node can include a complementary feature that couples to the engagement features of the garment. The engagement feature and the complementary feature can be coupled and decoupled by a user.

The problem of decoupling a sensor and recoupling the sensor such that the sensor position is accurately maintained at a site (at a location on a patient's body) can be solved by including the engagement feature on the garment, and/or the sensor shape, that is configured to be positioned at a location on a patient's body. For instance, a chest strap can be configured to encompass a patient at the location of the chest. The location of the sensing device can include a site positioned along the location. The site is a smaller, more specific position on the body. The engagement feature can be in fixed alignment with the site, such as aligned over a patient's collarbone. In one example, the garment is configured to maintain a location on the patient's body, and the engagement feature is in fixed alignment with the garment. Accordingly, the sensor module can be coupled to the garment at a site corresponding to the engagement feature. The complementary feature can decouple from the engagement feature such that the sensor module can be removed from the garment, and the garment location can be maintained on the patient. The sensor module can be recoupled to the garment, such as by coupling the complementary feature of the sensor module to the engagement feature of the garment. The engagement remains in fixed relation with the site, and the reattached sensor module can be positioned at the site for further measurement of physiological parameters.

The problem of collecting accurate data from the sensor can be solved by a sensor that provides electrical output based on information corresponding to the engagement feature. In one example, the output of the sensor module can be based on the site information corresponding to the engagement features. For instance, the sensor module can detect (e.g., by reading a signal of an RFID chip or other manner of identification) the site (e.g., proximal right biceps) of the engagement feature. The sensor can be placed at a plurality of locations on the body. The output of the sensor can be affected by the physiological parameters of the body associated with the site of the sensor. The sensor can be calibrated to include information based on a physiological parameter associated with site information corresponding to the engagement feature. Stated another way, the output of the sensor can be adjusted depending upon the site of the engagement feature that the sensor module is coupled to.

The problem of charging the sensor without a wired connection can be solved by including an induction coil within the sensor module such that the sensor module can be charged without a wired connection.

The problem of coupling and decoupling a sensor module from a body can be solved by including an engagement feature on a membrane. The membrane includes a contact side and an opposing side. The contact side is configured to conform to a tissue surface. In one example, the contact surface can include adhesive for coupling the sensor module to the body. The complementary feature of the sensor module can couple and decouple with the engagement feature of the membrane. For instance, the membrane can remain coupled to the body and the sensor module can be decoupled from the membrane (e.g., for charging, cleaning, etc.). Examples of an engagement feature include a user operable clip, a snap, a pin, a magnet, a hook and loop fastener, a zipper, a press-fit, a snap-fit, a quick release fastener, or the like. An engagement feature can be configured to retain the sensor module to the membrane. In one example, the membrane includes an aperture and a pocket. The aperture can be aligned with the pocket and configured to receive the sensor module. The pocket can include fixed walls and the aperture can be configured to allow the passage of the sensor module.

The problem of removing a sensor coupled to a body by adhesive without causing pain or injuring a patient can be solved by a membrane including a channel having a first port on the contact side and having a second port on the opposing side. For instance, the membrane can include a porous substrate. The channel can be configured to convey or disperse an adhesive solvent from the opposing side to the contact side. The solvent can be operable to decouple the sensing device from the body of the patient. In one example, the membrane can include a solvent reservoir. The solvent reservoir can include the adhesive solvent. The adhesive located on the contact side of the membrane can be isolated from the solvent by a removable barrier. The user can reposition the removable barrier to apply the solvent to the adhesive. In one example, the membrane can include a notch or expansion slot configured to allow the membrane to flex in order to conform to the tissue surface.

One example includes optics that protrude from a surface and exerts a pressure on the tissue site. One example includes light absorbing materials that reduce (or minimize) ambient and piped photons. One example includes foam backing material (sometimes referred to as a filler).

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Described herein are various configurations of devices, systems, and methods of using a sensing device, such as a physiological sensing device. The following examples and drawings illustrate the present subject matter to enable those skilled in the art to practice the subject matter described in the following detailed description. Portions and features of some examples may be included in, or substituted for, those of other examples.

Blood oxygenation is commonly measured using a pulse oximetry sensor positioned on a finger, a toe, or an earlobe of a patient. The pulse oximetry sensor is held in position with a spring-loaded clip.

A number of complications are associated with a traditional clip-attached pulse oximeter. For example, the clip can interfere with routine activities and is prone to damage.

An example of the present subject matter is configured to position a sensor at a particular site and configured to exert a positive pressure on the sensor module.

An example of the present subject includes a body-worn sensor. A body-worn sensor, according to one example, includes a garment fitted with an attachment module. The attachment module is configured to receive a sensor module. The garment, the attachment module, and the sensor module are configured to ensure that the sensor module is held firmly in contact with the tissue at the measurement site. In one example, this includes a garment having an elastic member that provides a force to exert pressure on the sensor at the tissue site. In another example, the garment includes an inelastic member and the attachment module is fitted with a clutch or a slip-joint that ensures adequate applied pressure and ensures that the applied pressure is not excessive.

In one example, the garment or the membrane (as described herein) is configured to apply a pressure on the sensor module at the tissue site. In one example, the garment (such as a belt) is coupled to an attachment module in a manner that allows the garment tension to apply a pressure. The belt can be coupled to the attachment module at a location that is spaced apart from a sensing surface of the sensor module. In this manner, with increasing tension on the belt, the sensor module is thrust into the tissue site with increasing pressure. In another example, the attachment module is coupled to a pad (or membrane). The pad is affixed at a tissue site by an adhesive on a contact surface. The attachment module is coupled to the pad in a manner that positions a sensing surface of the sensor module below a contact surface of the pad, and thereby exert a suitable applied pressure at the tissue site.

In one example, the clips and other mechanisms (described in the context of the engagement feature and the complementary feature) are configured to rigidly secure the sensor module in the attachment module. The engagement feature and the complementary feature are configured to maintain the sensor module in a fixed position notwithstanding application of the pressure between the sensor module and the tissue site.

One example of the present subject matter is configured to exert a pressure between the sensor module and the tissue site wherein the applied pressure falls in a specified range. If the applied pressure is too great, then the tissue site is at risk of complications, such as pressure necrosis. If the applied pressure is insufficient, then the data from the sensor module may not be meaningful or accurate. One example includes a sensor fitted to the sensing surface of a sensor module that provides a measure of the applied pressure. One example is configured to measure an amplitude or other parameter of an AC signal component and compare the AC signal component with a threshold value or values.

A display coupled to the sensor module can provide an indication of the measured pressure relative to a predetermined pressure range of predetermined pressures. The display can include a light emitter, such as a yellow light corresponding to insufficient pressure, a green light corresponding to a satisfactory pressure, and a red light corresponding to excessive pressure.

Figure 1:
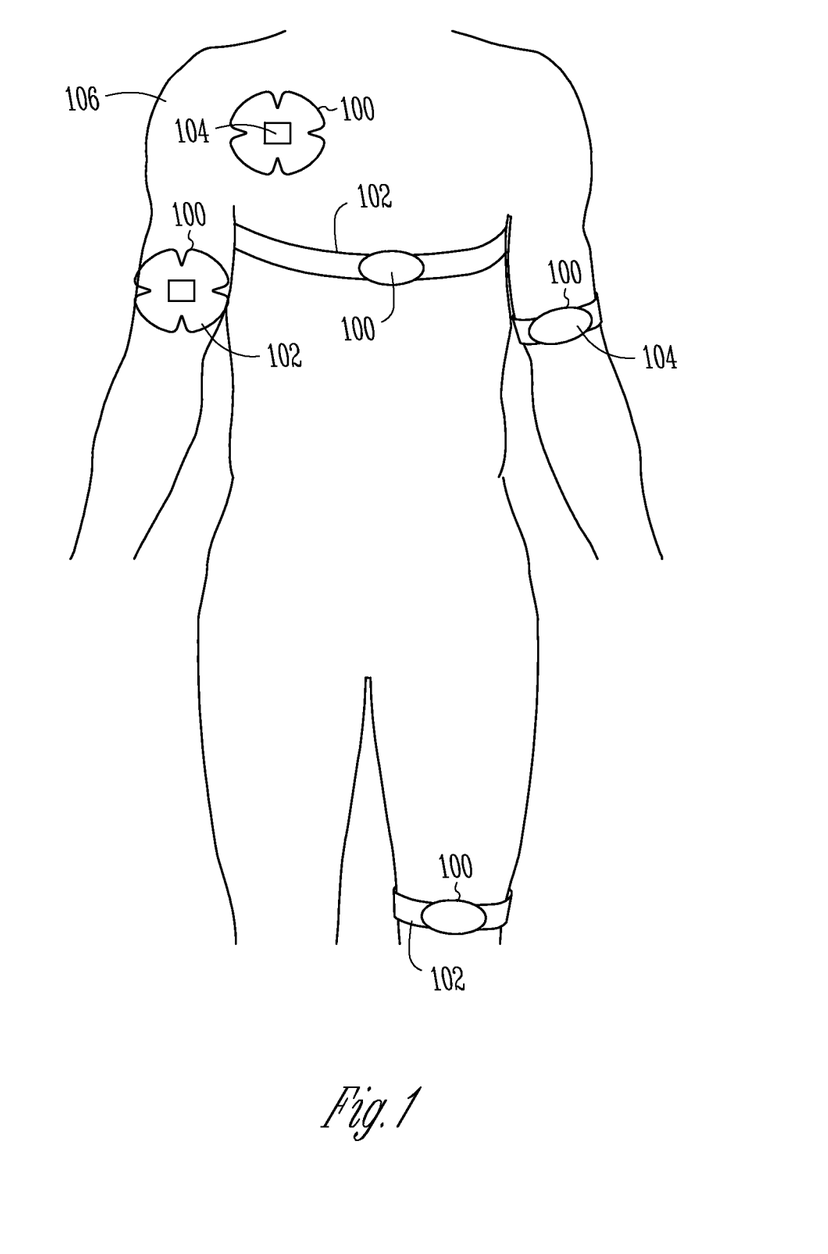
FIG. 1 shows one example of a body with a plurality of sensing devices coupled thereto.

FIG. 1 shows one example of a body with a plurality of sensing devices 100 coupled thereto. The sensing device 100 includes a garment 102 and a sensor module 104. The sensing device 100 can be coupled to a body 106 (e.g., a body 106 of a patient) for monitoring physiological parameters associated with the patient. The sensing device 100 can be positioned at a location on the patient. For instance, the garment 102 can be coupled to the body 106 at the location. The garment 102 can encompass a location on the body.

A garment, such as garment 102, can include, but is not limited to, an article of clothing, such as a shirt, pants, headband, armband, chest strap, leg band, a sleeve, a strap, an adhesive patch, a brassiere, or the like. In one example, garment 102 is patient conformable. The location can include, but is not limited to, an arm, torso, chest, leg, head, or the like. In one example, the garment 102 can be configured to couple to a plurality of locations on a body 106. For instance, the garment 102 can be configured to have an adjustable member for coupling to the body 106, such as a strap or band with an adjustable fastener. The length of the adjustable member can be configured by the user for coupling to a location on the body 106, such as by repositioning the adjustable fastener along the length of the adjustable member. In one example, the garment 102 can be configured for a specific location on the body 106, such as a hat, a sleeve, a brassiere, a waistband in pants, a headband, an armband, a leg band, or the like. As shown in FIG. 1, there are three sensing devices 100 coupled to the body 106 at a plurality of locations, including the chest, arm, and leg respectively.

The garment 102 can be coupled to the body 106 by friction. For instance, friction from pressure applied to the body 106 by the garment 102. In one example, the pressure can be exerted on the body 106 by a garment 102 that fits tightly against the body 106. For instance, a garment that includes a band that is smaller than the distance around the location (e.g., chest, arm, leg, or head circumference).

In one example, the garment 102 includes an inelastic member. Pressure can be applied to the body 106 by adjusting the length of the garment 102 to be smaller than the distance around the location. In one example, the garment 102 can include an elastic material the can be stretched around a location, such as to encompass the location. Materials of the garment can include, but are not limited to, cotton, polyamide, polyester, other polymer, or the like. The material can be formed into a strap, band, woven fabric, webbing, knit, or the like.

FIG. 1 illustrates a device 100 at a collar bone region and having sensor module 104 affixed using a patch (or membrane). The figure also shows a device 100 at a forearm region and attached using garment 102 (here indicated as a patch or membrane).

Figure 2:
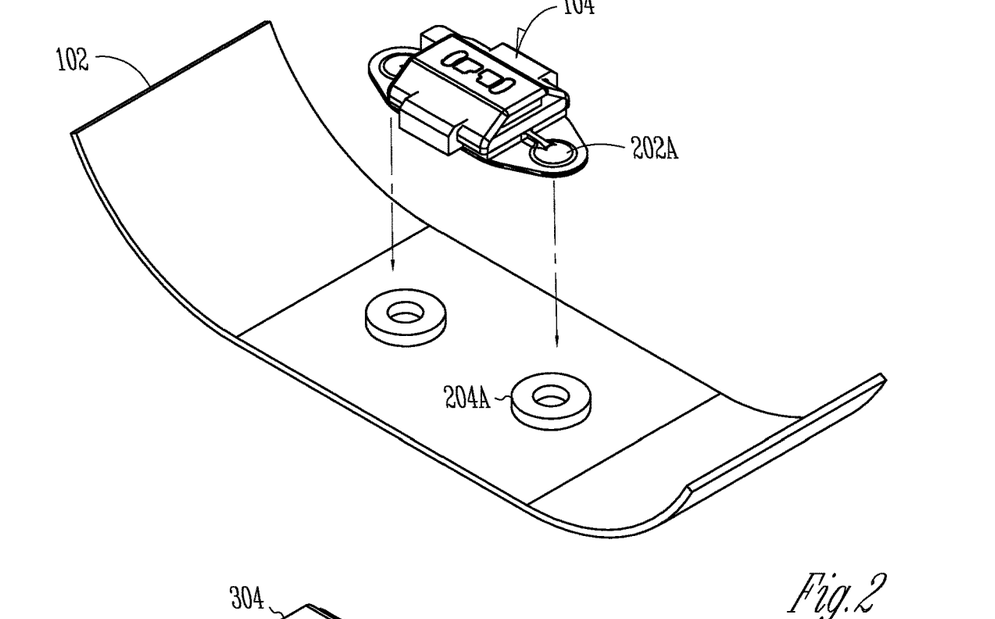
FIG. 2 shows a perspective view of one example of a garment including engagement features and a sensor module including complementary features configured to couple and decouple with the engagement features.

FIG. 2 shows a perspective view of one example of a garment 102 including an engagement feature 202A (e.g., two as shown in FIG. 2) and a sensor module 104 including a complementary feature 204A (e.g., two as shown in FIG. 2) configured to couple and decouple with the engagement features 202A. The sensor module 104 can be attached to the garment 102 by coupling the complementary feature 204A with the engagement feature 202A.

Figure 12:
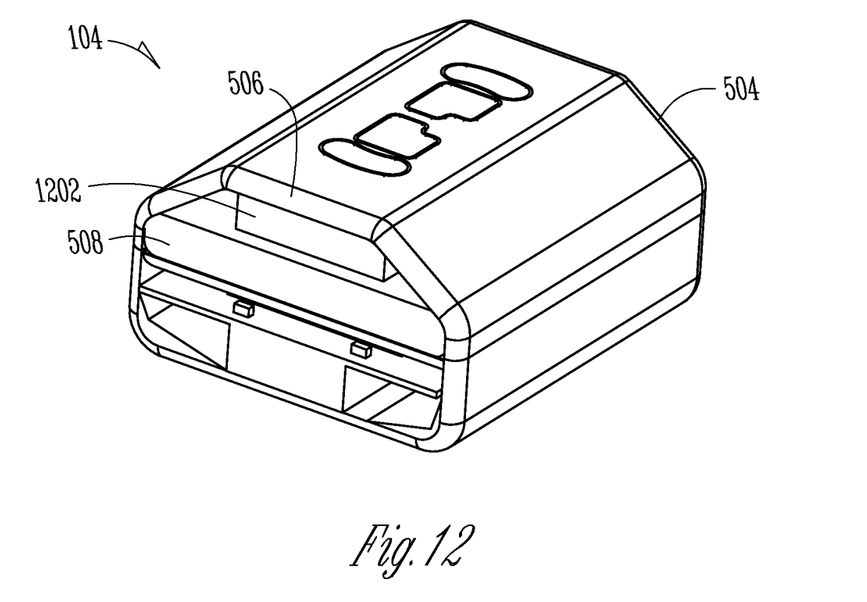
FIG. 12 shows a perspective view of a sensor module.

The sensor module 104 includes a sensor, housing, tissue pad, garment pad, filter, battery, and a node (some of which are shown in FIG. 12 and described herein). The sensor module 104 can be configured to provide an electrical output on a node. The electrical output can include a wired signal on the node, a wireless signal, data stored on a non-transitory computer readable media, or the like. In one example, the output includes a measure of a physiological parameter associated with the body 106. The physiological parameter can include, but is not limited to, heart rate, blood pressure, temperature, electrocardiogram signal, oxygenation (such as SpO2), carboxyhemeglobin, methemeglobin, blood glucose, total hemeglobin, hematocrit, or the like. In one example, the sensor is a photoplethysmogram (PPG) sensor.

The node can include a segment on an electrical circuit included in the sensor module 104. For instance, the node can include an electrical connector, antenna, electrical lead, memory module, processor, or the like. The sensor 104 can wirelessly transmit an electrical output on the node (e.g., using wireless antenna). In one example, the sensor module 104 can include a logic circuit configured to produce the electrical output on the node. The electrical output can be based on a measure of a physiological parameter associated with the body 106.

In one example, the sensor module 104 can include a processor. The processor can include instructions thereon to produce an output based on a measure of a physiological parameter associated with the body 106.

In one example, the electrical output includes a measure of a physiological parameter associated with the body, and the output is based on site information corresponding to the engagement feature 202A. The location of the sensing device 100 includes a site that is positioned along the location. For instance, the site is a small portion of the location at which the sensor can detect physiological parameters. For instance, the site can include a portion of the body 106 positioned over a vein or artery. In one example, the site is near a collar bone.

The position of the engagement feature 202A can correspond to the position of the site. Accordingly, the sensor can measure the physiological information of the body 106 at the site. In one example, the sensor can detect site information, such as site information included on the engagement feature 202A or garment 102. In one example, the sensor module 104 can read the site information included in the engagement feature 202A or garment 102 and base the electrical output on the site information included in the engagement feature 202A or garment 102. Basing the electrical output on the site information can include, but is not limited to, transmitting the site location information, transmitting a transformation of the measure of the physiological parameter associated with the body, transmitting the physiological parameter, transmitting a calibration coefficient, transmitting the physiological parameter as a function of a calibration coefficient. A calibration coefficient can include at least one of an integer or a function. In one example, the electrical output of the sensor module 104 can be based on a product, sum, or function of the calibration coefficient and the measurement of the physiological parameter.

The engagement FIG. 202A can include, but is not limited to, a snap, pin, magnet, adhesive, a clip, a pocket, a hook and loop fastener, a zipper, a press fit, a snap fit, a quick-release fastener, or the like. In one example, the engagement feature 202A can include an elastic clip, such as a flexible retainer that fastens the sensor module 104 to the garment 102. The elastic clip can be coupled to the garment 102 (e.g., stitched to the garment or coupled with adhesive) and coupled to the sensor module 104, such as a latch with mating features on the sensor module 104. In one example, the garment 102 can include a bracket. The bracket can hold the sensor module 104, such as by retaining the sensor module 104 with fixed walls positioned on the bracket. The elastic clip can couple to the engagement feature 202A in order to encompass the sensor module 104 between the bracket and the elastic clip and thereby retain the sensor module 104 to the garment 102.

The engagement feature 202A can be in fixed alignment with a site and the sensor module can be in fixed alignment with the engagement feature 202A. For instance, the garment 102 can hold a position at a location on the body 106. The engagement feature 202A can be in fixed alignment with the garment 102. As shown in FIG. 2, the engagement feature 202A includes a snap that is in fixed alignment with the garment 102. The engagement feature 202A can be held in fixed alignment with the garment 102 by a fastener. The fastener can include, but is not limited to, at least one of a nail, tape, thread, adhesive, rivet, hot weld, hook and loop fastener, press-fit, pin, a magnet, or the like.

The sensor module 104 can include a complementary feature 204A that is coupled to the sensor module 104 by adhesive, insert molding, press-fitting, magnets, pins, rivets, screws, or the like. The complementary feature 204A can couple and decouple with the engagement feature 202A, such as without the use of a tool. Accordingly, the complementary feature 204A can include, but is not limited to, at least one of a snap, pin, magnet, hook and loop fastener, zipper, press-fit, snap-fit, quick release fastener, or the like.

Due to the fixed alignment of the engagement feature 202A with the garment 102, the sensor can be positioned to measure physiological parameters of a body at a site. For instance, the complementary features 204A can be in fixed alignment with the engagement features 202A, thereby fixing the position of the sensor at the site. The sensor module 104 can be decoupled from the garment 102 and the garment 102 can remain in place on the body 106. In one example, the sensor module 104 can be recoupled to the garment 102 by coupling the complementary features 204A of the sensor module 104 to the engagement features 202A of the garment 102. Because the garment 102 remains in place at the location on the body 106 and the engagement feature 202A is positioned in fixed alignment with the garment 102, the sensor module 104 (and the sensor) can be realigned with the site.

Figure 3:
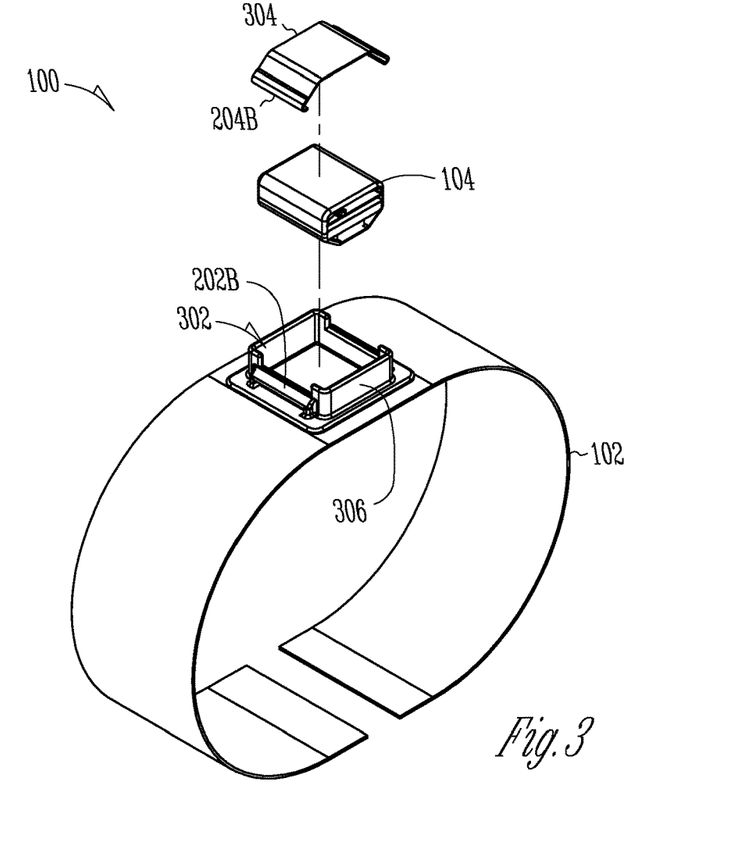
FIG. 3 shows a perspective view of one example of a sensing device including a dock with engagement features and an elastic clip with a complementary feature for securing the sensor module to the garment.

FIG. 3 shows a perspective view of one example of the sensing device 100 including a dock 302 in fixed alignment with the garment 102 and an elastic clip 304 that engages with the dock 302 to retain the sensor module 104. As shown, in one example, the garment 102 can include a wrist band for coupling to the forearm or wrist of a patient's body 106. The wrist band can encompass the body 106. In one example, a garment can be configured as a band suitable for encircling other portions of a body, such as a bicep, a thigh, or a calf. In the example shown, dock 302 can be described as 'top loading' and garment 102 can include a band for coupling to a limb of a patient.

The dock 302 can include a plurality of retaining features 306 configured to engage with the sensor module 104. The retaining feature 306 can include a rib, wall, lug, peg, or other feature that is attached to the dock 302 and positioned to restrain the movement of the sensor module 104 along the garment 102. As shown, the dock 302 can include an engagement feature 202B. The engagement feature 202B can include a latch, hook, or any of the engagement features 202A previously described herein. As previously described, the engagement feature 202B can be in fixed alignment with the garment 102.

The elastic clip 304 can include one or more complementary features 204B as shown in FIG. 3. The elastic clip 304 can include a sheet of material that is formed to retain the sensor module 104 to the dock 302 with at least one complementary feature 204B. The material of the clip can includes, but is not limited to, steel, aluminum, polymer, fabric, sheet, or the like. The complementary feature 204B can be included on the end of the elastic clip 304 and can include a latching feature for coupling to the engagement features 202B. As shown in FIG. 3, the elastic clip 304 includes one complementary feature 204B on each end of the elastic clip 304. The complementary features 204B can be coupled with the engagement features 202B. In one example, the elastic clip 304 can be molded or formed to retain the sensor module 104 between the dock 302 and the elastic clip 304. In one example, the complementary feature 204B can be decoupled from the engagement feature 202B without the use of a tool. In one example, elastic clip 304 includes a band of formed metal and is configured in a manner to exert a tension force to retain sensor module 104 in a fixed relation with garment 102. Elastic clip 304 can be referred to as a tension band and can have clips that engage with a corresponding feature, such as feature 202B. Garment 102 can include a strap.

In one example, the dock 302 or retaining feature 306 can include an operable door. A first end of the door can be coupled to the dock 302 with a hinge. The door can include a latch at a second end. The latch can be configured to couple to the dock 302 and retain the sensor module 104 between the door and the dock 302.

Figure 4:
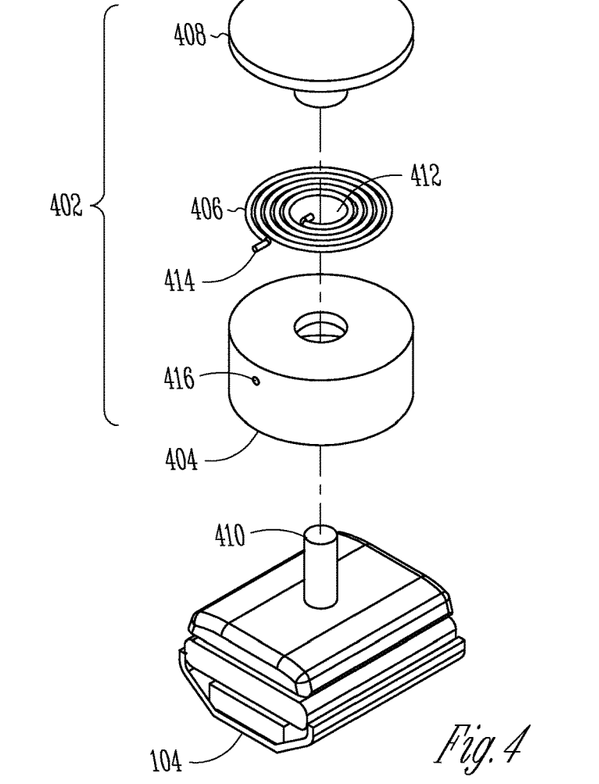
FIG. 4 shows a perspective view of one example of a sensing device including a torque limiting fastener.

FIG. 4 shows a perspective view of one example of a sensor module 104. Sensor module 104 can be coupled to garment 102 (not shown in this view) with a user operable control, such as a torque limiting fastener 402. The engagement feature 202 (e.g., 202A-B in FIG. 2) can include a user operable control. The user operable control can be configured to selectively position the sensor module 104 relative to the garment 102. In one example, the user operable control includes a torque limiting element (e.g., a torque limiting fastener 402). As shown in FIG. 4, the torque limiting fastener 402 can include a fastener housing 404, torsion spring 406, and knob 408. The sensor module 104 can include a threaded rod 410. The engagement feature 202 (e.g., 202A-B) can include the fastener housing 404, such that the fastener housing 404 is in fixed relation to the garment 102. In one example, the threaded rod 410 can be movably coupled with the fastener housing 404 such that a user can adjust the position of the sensor module 104 with respect to the garment 102. In one example, the sensor module 104 can rotate and translate with respect to the garment 102. For instance, the sensor module 104 can translate in a direction that is normal to the surface of the garment 102 or normal to the body 106.

In one example, the description here concerning engagement feature 202 (such as feature 202A) also applies to complementary feature 204 (such as feature 204A).

The position of the sensor module 104 can be adjusted by the user with the actuator knob 408. The threads of the threaded rod 410 can engage with complementary threads on the fastener housing 404. The actuator knob 408 can be coupled to the threaded rod 410 with the torsion spring 406. For instance, the torsion spring 406 can be coupled to the actuator knob 408 and releasably coupled to the threaded rod 410, such that a rotation of the actuator knob 408 rotates the threaded rod 410 with respect to the fastener housing 404. The rotation of the threads on the threaded rod 410 with respect to the threads of the fastener housing 404 results in a translation and rotation of the sensor module 104 with respect to the garment 102.

As shown in FIG. 4, the torsion spring 406 includes a first leg 412 at the center of a coil of the torsion spring 406 and a second leg 414 along the perimeter of the coil. The first leg 412 engages with the actuator knob 408. In one example, the second leg 414 engages with a port 416 in the fastener housing 404. The coil of the torsion spring 406 reduces in diameter as the actuator knob 408 is rotated and torque is applied to the threaded rod 410. The reduction in the diameter of the coil is proportional to the torque applied to the actuator knob 408. The second leg 414 can disengage from the port 416 of the fastener housing 404, such as when a sufficient torque is applied to the actuator knob 408 to reduce the coil diameter to an extent that the second leg 414 disengages from the port 416. Stated another way, the tension of the torsion spring 406 pulls the second leg 414 from the port 416. One example includes disengagement of the second leg 414 from the port 416.

The user operable control can permit the user to position the sensor module 104 with respect to the garment 102. In one example, the user operable control (e.g., the torque limiting fastener 402) can be used to apply a specific pressure between the sensor module 104 and the tissue of a body 106. For instance, the rotation of the actuator knob 408 translates the sensor module 104 toward the body 106 relative to the garment 102. This can increase the pressure applied to the sensor module 104 by the garment 102. Stated another way, the user operable control can adjust the garment 102, such as to increase the tension on the garment 102 (e.g., tighten the garment 102).

An increase in tension on the garment 102 increases the torque on the actuator knob 408 which reduces the coil diameter of the spring 406. When the tension of the garment is at the maximum desired amount, the coil size will be small enough to disengage the second leg 414 from the port 416. This disengagement of the second leg 414 from the port 416 allows the actuator knob to rotate without applying additional tension on the garment 102.

In one example, sensor module 104 is positioned in a manner that applies a pressure to body 106. If the applied pressure is insufficient, then the AC signal component from the sensor may be inadequate to accurately determine a physiological parameter such as oxygenation. If the applied pressure is too large, then the tissue is at risk for a medical complication such as pressure necrosis. In one example, sensor module 104 is fitted with a clutch that has a set-point that precludes application of excess pressure.

Figure 5:
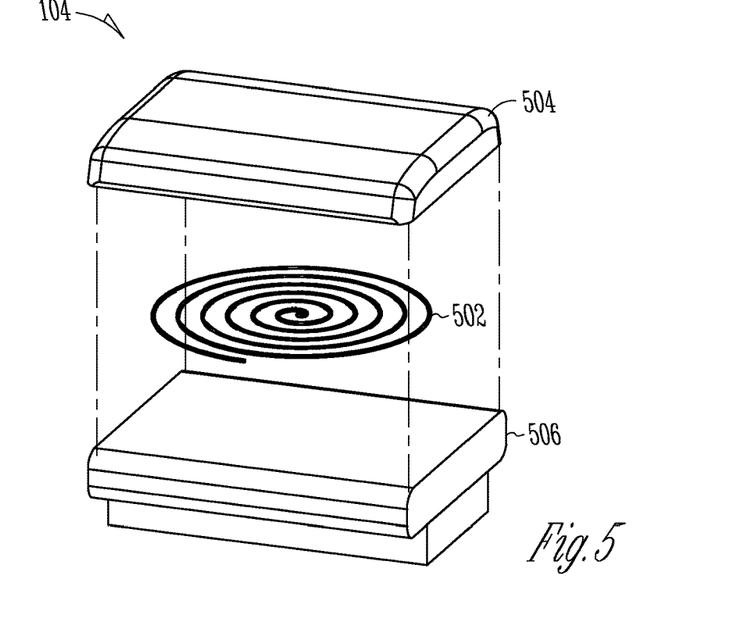
FIG. 5 shows a perspective view of one example of a sensor module including an inductor.

FIG. 5 shows a perspective view of one example of a sensor module 104 including an inductor 502. In one example, the sensor module 104 can include a sensor housing 504, a sensor 506, and an inductor 502. The inductor 502 can be electrically coupled to the sensor 506, such as to wirelessly convey electric power to the sensor 506. In one example, a capacitor can be used to wirelessly convey electric power to the sensor 506. The sensor housing 504 can support the sensor 506 and one or more of the inductor 502 or capacitor within the sensor module 104. Inductor 502 can include an inductive charging coil. One surface of sensor 506 is configured as a sensor-patient interface.

Figure 6:
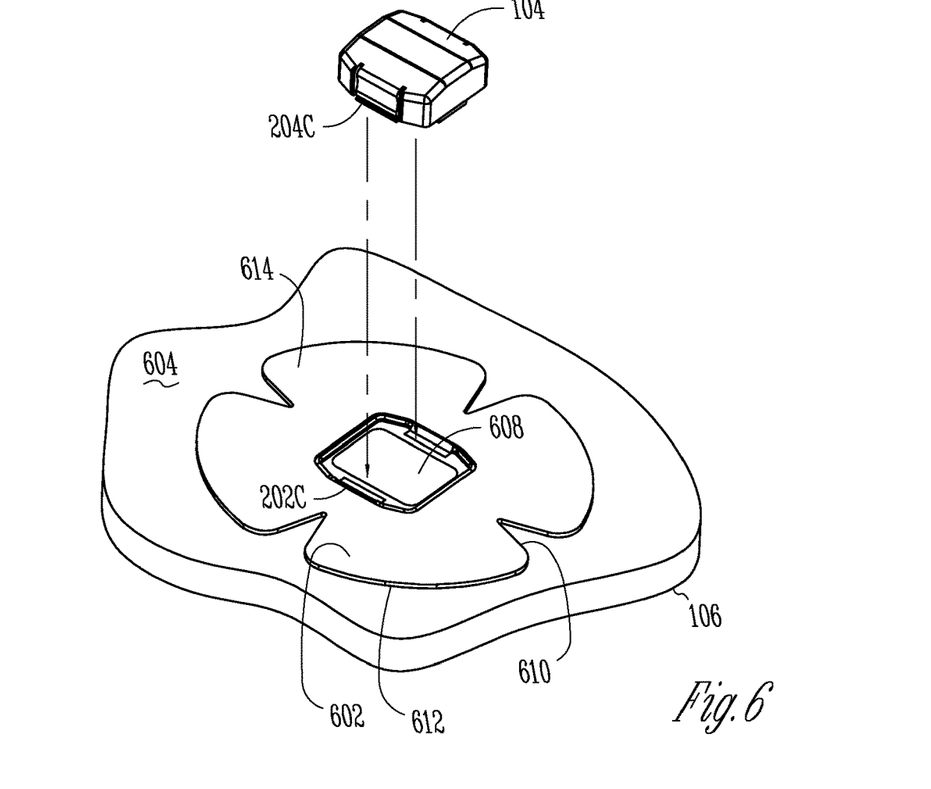
FIG. 6 shows a perspective view of one example of a membrane including an engagement feature and a sensor module including a complementary feature.

FIG. 6 shows a perspective view of one example of a membrane 602 including an engagement feature 202C and a sensor module 104 including a complementary feature 204C. The membrane 602 includes a contact side 612 and an opposing side 614. The contact side 612 can be configured to conform to a tissue surface 604 of the body 106. The membrane 602 can include at least one engagement feature 202C, as previously described with regard to FIGS. 1-5. As shown in FIG. 6, the membrane 602 can include an aperture 608. The sensor module 104 can measure physiological parameters through the aperture 608. The membrane can include at least one notch 610 configured to allow flexure of the membrane 602, such that the membrane 602 can conform to the tissue surface 604. In one example, the membrane 602 can include an expansion slot. For instance, the expansion slot can be stretched open so that the membrane 602 can expand or contour to a tissue surface 604. The figure illustrates a flat, disposable membrane including an engagement feature and a mating sensor module having a complementary feature.

In one example, the membrane 602 can include a biocompatible material including, but not limited to, at least one of a woven material, a non-woven material, foam, elastomer, textile, or the like.

The sensor module 104 can include at least one complementary feature 204C configured to couple and decouple with the engagement feature 202C. Complementary feature 204C can be configured to couple and decouple the sensor module 104 with the membrane 602 and can include adhesive alone or can include adhesive in addition to other complimentary features.

The engagement feature 202C and the complementary feature 204C can be configured to retain the sensor module 104 in fixed alignment with the membrane 602. Feature 204C, in the example shown, can be configured to receive two clips for engagement with other structure. For instance, the sensor module 104 can be decoupled from the membrane 602 while the membrane 602 remains attached to the tissue surface 604. The membrane 602 can be applied to the tissue surface 604 before the sensor module 104 is coupled to the membrane 602. This provides the advantage of coupling a membrane 602 to the tissue surface 604 in a manner such that the membrane 602 conforms to the tissue surface 604. The membrane 602 can couple the sensor module 104 to the body 106 with a greater pressure between the sensor module 104 and the tissue surface 604 as a result of the degree of conformity between the tissue surface 604 and the membrane 602. Increased pressure between the sensor module 104 and the tissue surface 604 can provide improved sensor contact (e.g., improved accuracy of the physiological parameter measurement). Membrane 602 can include a pad of fabric, textile, or elastomeric material that allows conformance with the skin at tissue surface 604. Membrane 602 can be bonded to the skin (tissue) with an adhesive.

Figure 7:
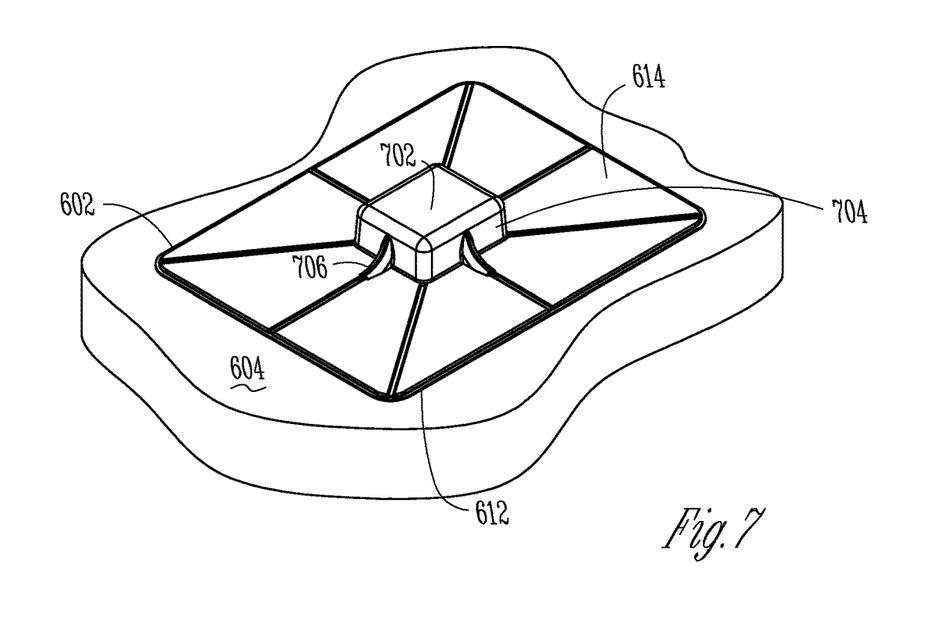
FIG. 7 shows a perspective view of one example of a membrane including a pocket with fixed walls configured to receive the sensor module.

FIG. 7 shows a perspective view of one example of a membrane 602 including a pocket 702 with fixed walls 704 configured to receive the sensor module 104. The membrane 602 can include an aperture 608 (FIG. 6) and a pocket 702 aligned with the aperture 608. The pocket 702 can be configured to receive the sensor module 104 through the aperture 608. The figure illustrates one example of a formed, disposable membrane including a plurality of flexibility channels, vertical support ribs, and a pocket with fixed walls configured to receive the sensor module.

The contact side 612 can be configured to receive an adhesive coating. The adhesive coating can bond the membrane 602 to the tissue surface 604. In one example, the sensor module 104 can be retained within the aperture 608 and between the pocket 702 and the tissue surface 604.

As shown in FIG. 7, the membrane 602 can include at least one support rib 706 positioned between the opposing side 614 and the pocket 702. The support rib 706 provides structural strength to the pocket 702, such as to increase the pressure applied to the sensor module 104 between the pocket 702 and the tissue surface 604 by increasing the rigidity of the pocket 702. Stated another way, a support rib 706 is configured to transfer force from the tissue surface 604 (e.g., through the adhesive bond) to the sensor pocket 702. In one example, the support rib 706 can reduce stretching of the tissue surface 604 resulting from the pressure between the sensor module 104 and the pocket 702 (e.g., pressure exerted on the adhesive bond of the contact side 612).

In the example shown in FIG. 7, the membrane 602 can be decoupled from the tissue surface 604 in order to replace the sensor module 104. Decoupling the contact surface 612 from the tissue surface 604 can include disbonding the adhesive between the contract surface 612 and the tissue surface 604.

Figure 8:
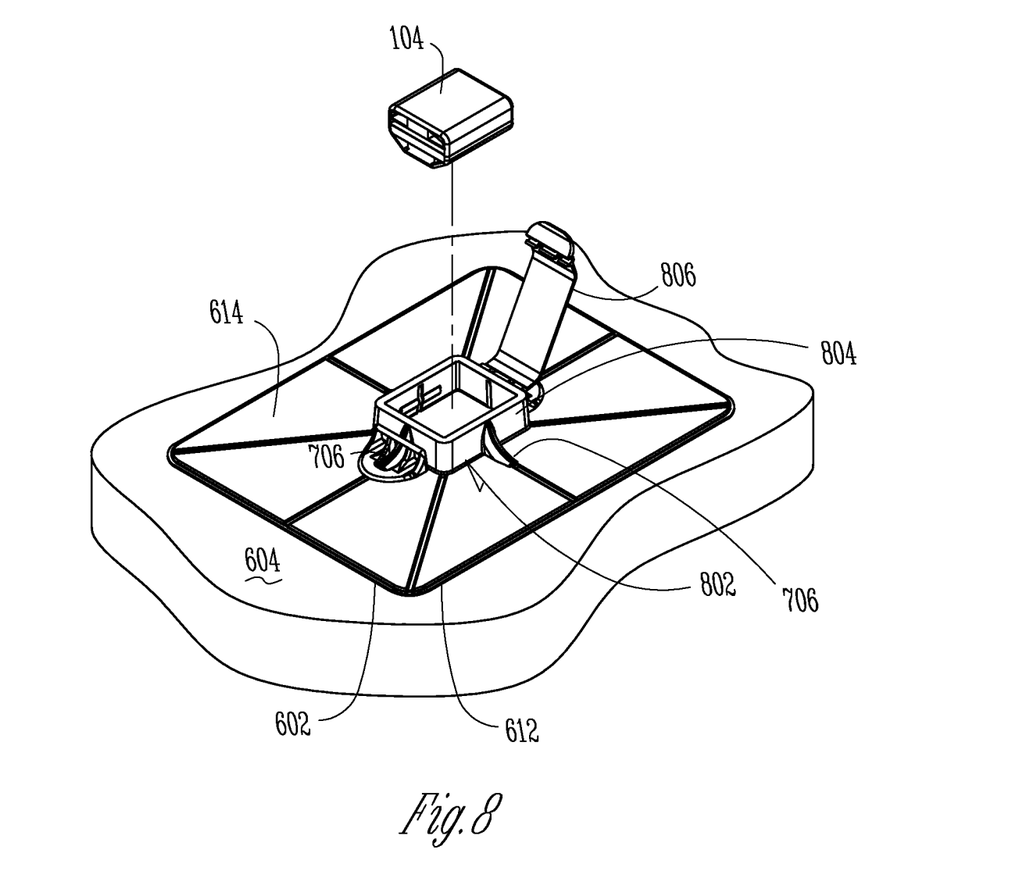
FIG. 8 shows a perspective view of one example of a membrane including a user operable clip.

FIG. 8 shows a perspective view of one example a membrane 602 including a user operable door 806 (e.g., an elastic clip 304 as previously shown in FIG. 3 and described herein). Door 806 can be called a retainer. The membrane can include a bracket 802. As shown in FIG. 8, the bracket 802 can include fixed walls 804. The fixed walls 804 can maintain the position of the sensor module 104 along the membrane 602. In one example the bracket 802 and the membrane 602 can be formed as a single component. The membrane 602 can include at least one support rib 706 positioned between the opposing side 614 and the fixed walls 804. The figure illustrates one example of a formed, diposable, "top loading" membrane including a user operable clip.

As previously mentioned, the example shown in FIG. 8 includes an operable door 806. The operable door 806 can include, but is not limited to, an elastic element, an elastic clip (e.g., elastic clip 304), a user-operable clip, or the like. A first end of the operable door 806 can be coupled to the bracket 802 with a hinge. A second end of the operable door 806 includes a latch configured to engage with a receiving element included on the bracket 802. In one example, the latch can be included on the bracket 802 and the receiving element can be located on the second end of the operable door 806. The operable door 806 can be configured to retain the sensor module 104 between the operable door 806 and the tissue surface 604. One advantage to the operable door 806 is the ability for a user to decouple the sensor module 104 from the membrane 602 without disbonding the adhesive located between the contact surface 612 and the tissue surface 604.

Figure 9:
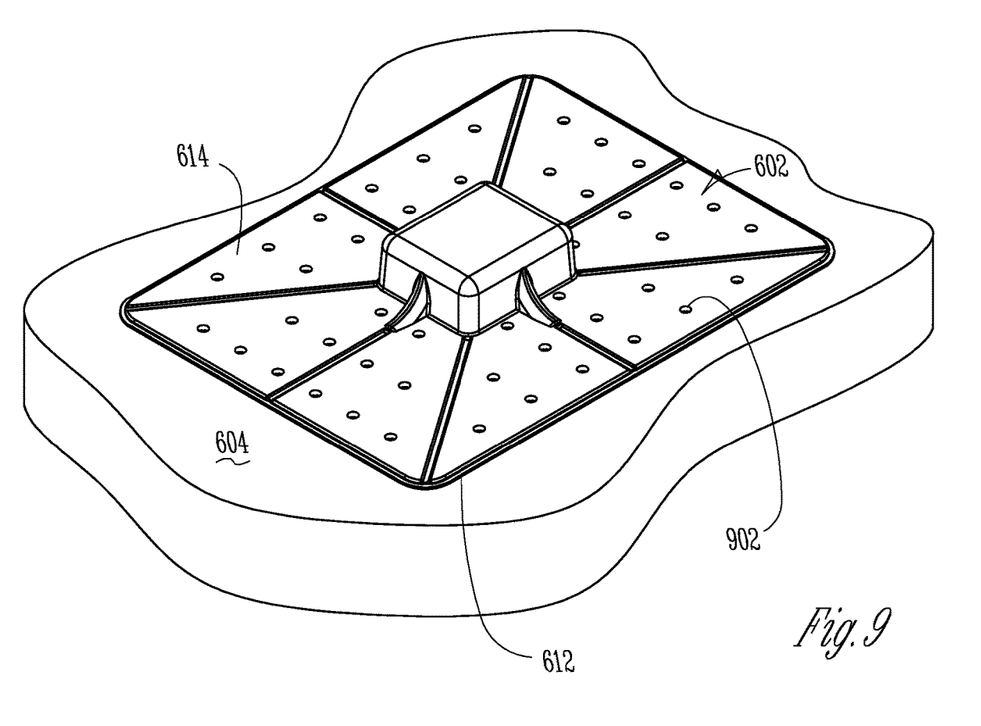
FIG. 9 shows a perspective view of one example of a membrane including a plurality of channels with a first port on the contact side of the membrane and having a second port on the opposing side.

FIG. 9 shows a perspective view of one example of a membrane 602 including a plurality of channels 902 with a first port on the contact side 612 of the membrane 602 and having a second port on the opposing side 614. In one example, the channel 902 is configured to convey an adhesive solvent from the opposing side 614 to the contact side 612. Disbonding the adhesive between the contact side 612 and the tissue surface 604 can be accomplished by the application of the adhesive solvent to the opposing side 614 and conveyance of the adhesive solvent through the channels 902. For instance, the membrane can be configured to absorb the adhesive solvent, such that the adhesive solvent saturates the membrane 602, thereby disbonding the adhesive along the entire contact surface 612. The adhesive can include a biocompatible adhesive having sufficient peel strength to couple the membrane 602 to the tissue surface 604, maintain the coupling when the pressure between the sensor module and the membrane is exerted, and can be easily removed with a biocompatible adhesive solvent. In one example, the membrane 602 can be fabricated from a porous substrate, non-woven fibers, or other material. In one example, the channels 902 can be formed from pores included within the membrane 602. The figure illustrates one example of a membrane including a plurality of flexibility channels, and vertical support ribs, with a first port on the contact side of the membrane and having a second port on the opposing side.

Figure 10:
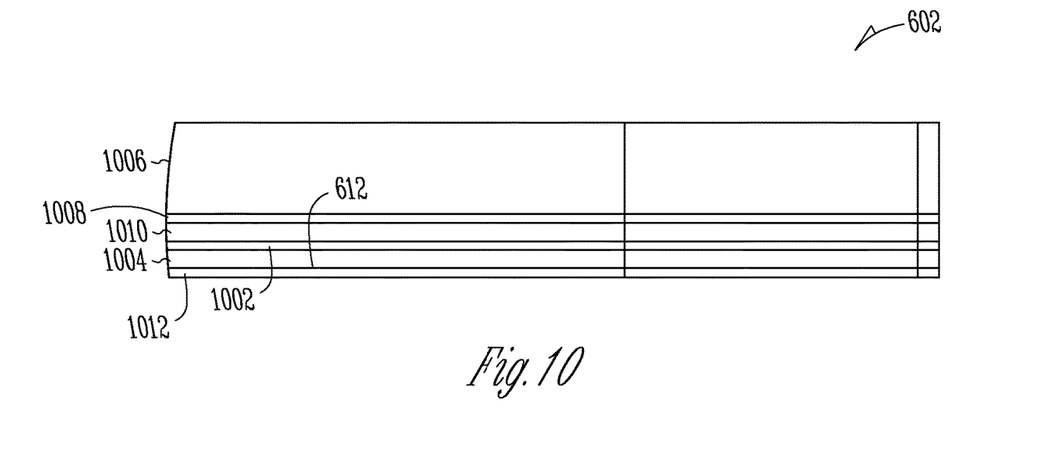
FIG. 10 shows a cross section view of a membrane including a solvent reservoir and a removable barrier.

FIG. 10 shows a cross section view of a membrane 602 including a solvent reservoir 1002 and a removable barrier 1004. The membrane 602 can include at least a substrate layer 1006, a first adhesive layer 1008, a liner 1010, a solvent reservoir 1002 (e.g., solvent layer), a barrier 1004, and a contact side 612 including a second adhesive layer 1012 that couples the membrane 602 to the tissue surface 604. The substrate layer 1006 can include a foam layer.

The solvent reservoir 1002 can be coupled to the membrane 602 and the solvent reservoir 1002 can be fluidly coupled to the contact side 612. As shown in FIG. 10, a barrier 1004 can be included between the solvent reservoir 1002 and the contact side 612. The barrier 1004 can isolate the adhesive solvent from the second adhesive layer 1012. In one example, the barrier 1004 can be user removable such that the adhesive solvent is exposed to the second adhesive layer 1012 and the solvent can disbond the membrane 602 from the tissue surface 604 by dissolving the second adhesive layer 1012. Disbonding the second adhesive layer 1012 can prevent pain or injury to the tissue surface 604 as a result of removing the membrane 602 from the body 106. In one example, reservoir 1002 includes a catalyst.

Figure 11:
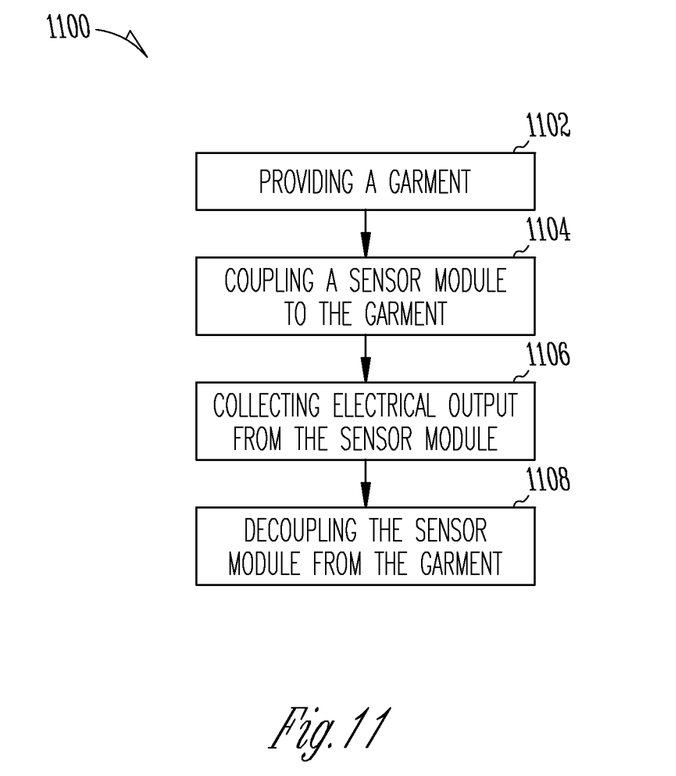
FIG. 11 shows a flow chart of one example of a method involving the sensing device.

FIG. 11 illustrates method 1100. At 1102, the method 1100 includes providing a garment 102. In one example, the garment 102 can be configured for a specific location on the body 106, such as a hat, sleeve, headband, armband, leg band, or the like. Materials of the garment 102 can include, but are not limited to, cotton, any woven or nonwoven fabric, polyamide, polyester, other polymer, or the like. The material can be formed into a strap, band, woven fabric, webbing, knit, or the like.

At 1104, the sensor module 104 can be coupled to the garment 102. The sensor module 104 can be attached to the garment 102 by coupling the complementary feature 204 (e.g., 204A-C) with the engagement feature 202 (e.g., 202A-C). The sensor module 104 can include a sensor 506, housing 504, tissue pad, garment pad, filter, battery, and node (as shown in FIG. 12 and described herein).

At 1106, the electrical output from the sensor module 104 can be collected, such as received by a data terminal (e.g., stored on a computing device). The sensor module 104 can be configured to provide an electrical output. The output can include a signal, wireless signal, data stored on a non-transitory computer readable media, or the like. In one example, the output includes a measure of a physiological parameter associated with the body 106. In one example, the sensor is a PPG sensor. In one example, the sensor module 104 can read the site information included in the engagement features 202A or garment 102 and include the site information in the electrical output.

At 1108, the method 1100 can include decoupling the sensor module 104 from the garment 102. For instance the complementary features 204 (e.g., 204 A-C) of the sensor module 104 can be decoupled from the engagement features 202 (e.g., 202A-D) of the garment 102.

In one example, sensor module 104 can be coupled or decoupled to the garment 102 without disturbing the coupling between the membrane 602 and body 106.

Figure 13:
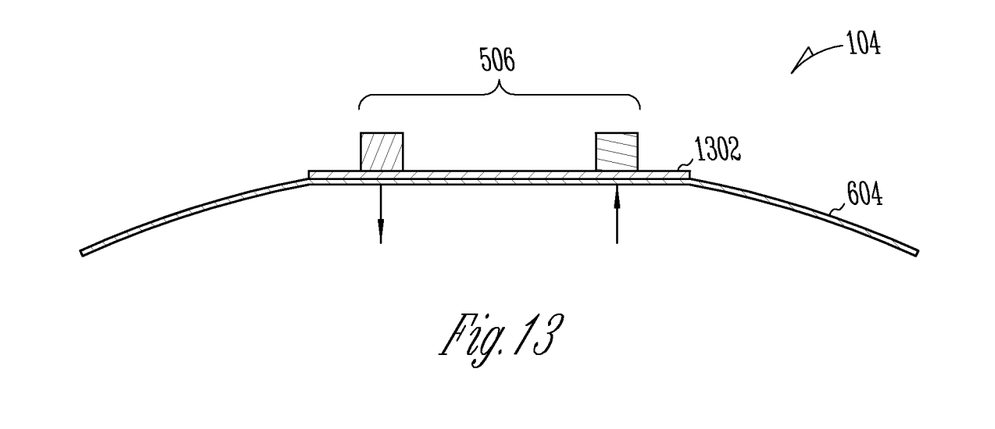
FIG. 13 shows a schematic view of one example of an optical filter included in the sensor module.

FIG. 12 shows a perspective view of a sensor module 104. As previously described, the module 104 can include a sensor 506, housing 504, tissue pad 1202, filter (as shown in FIG. 13 and described herein), battery 508, and a node (as previously described). The housing 504 retains the elements described above within the sensor module 104. In one example, the housing 504 can include a flexible material so the sensor module 104 can conform to the tissue surface 604. The tissue pad 1202 can be positioned between the sensor 506 and the tissue surface 604. In one example, the tissue pad 1202 conforms to the tissue surface 604, such as to provide a uniform pressure along the tissue surface 604 (e.g., exerted between the sensor module 104 and the tissue surface 604 by the garment 104). The tissue pad 1202 can include a sensor aperture allowing the sensor to measure the physiological parameters of the body 106. The application of uniform pressure to the tissue surface 604 improves the accuracy of the measurement of the physiological parameter. In one example, sensor module 104 is reusable.

The material of the tissue pad 1202 can include, but is not limited to, elastomeric foam, gel, air pillow, fluid pillow, or the like. The sensor 506 surface can include an optically opaque material to block ambient light from interfering with the measurement of the physiological parameter. The tissue pad 1202 can include a spring. In one example, at least one or more of a self-adjusting light emitting diode, photodiode, or sensor, can replace the tissue pad 1202, such as to substitute for the functionality of the tissue pad 1202.

FIG. 13 shows a schematic view of one example of an optical filter 1302 included in the sensor module 104. The optical filter 1302 can be coupled to the sensor module 104 between the sensor 506 and the tissue surface 604. In some instances, the optical filter 1302 can reduce the amount of light noise received by the sensor 506 and thereby improve the measurement of the physiological parameter. In one example, the optical filter 1302 can include a layer of polyimide (e.g., amber colored polyimide) in order to reduce the light noise. Filter 1302, in one example, includes a flexible circuit material such as Kapton. The figure illustrates a cross-sectional view of a light emitter (directional arrow showing light entering the tissue) and a light detector (direction arrow showing light exiting the tissue).

Figure 14:
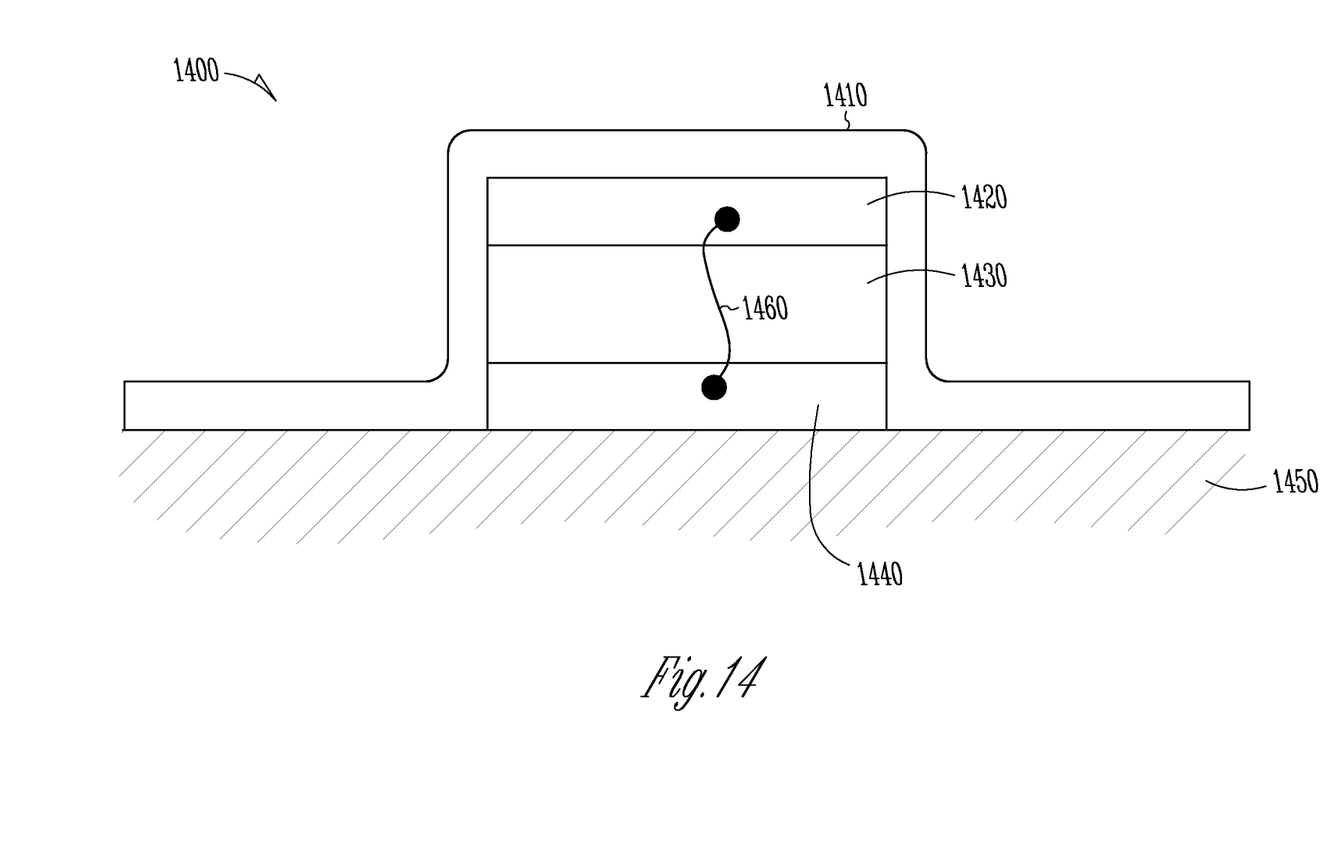
FIG. 14 illustrates a section view of a device having a filler, according to one example.

FIG. 14 illustrates a section view of device 1400 having a filler, according to one example. In this example, device 1400 is shown affixed to a site on tissue 1450. Device 1400 includes attachment mechanism 1410 which is attached to tissue 1450 by an adhesive, a garment (such as a shirt), a belt, a wrap, a patch, or other mechanism.

Attachment mechanism 1410 is configured to exert a compressive force between tissue 1450 and optics 1440. Optics 1440 can include any combination of a light source (such as an LED) and a light detector (such as a photodetector). Optics 1440 has a sensing surface (shown here to be flush, and in contact, with tissue 1450) and a non-sensing surface (shown here in contact with filler 1430).

Filler 1430 can include an elastic material that is moldable and compactable. In one example, filler 1430 includes a resilient foam (compressible under pressure and expands when pressure is removed).

Optics 1440 are electrically coupled to electronics 1420 by conductor 1460. Electronics 1420 can include a module having digital or analog circuitry. In various examples, electronics 1420 can include an amplifier, a filter, a signal conditioning circuit, a processor, a power supply, or other elements.

Conductor 1460 can include a flexible electrical connection that passes through filler 1430. In one example, conductor 1460 includes a flexible conductor having a strain relief feature (for example, a longer conductor than needed which is braided with Kevlar strand, the Kevlar strand is attached at both ends with slack in between).

Filler 1430 is configured to exert a compressive force (pressure) on the optics and is configured to ensure direct coupling between the optics 1440 and the skin of the user.

In one example, attachment mechanism 1410 includes a resilient material having an embedded electrical conductor. Examples of attachment mechanism materials can include lycra and rubber.

As noted, device 1400 is configured to ensure that the optics 1440 are held substantially in place relative to the skin (tissue 1450). A pressure applied by the combination of the attachment mechanism 1410 and the filler 1430 ensures good contact between the surfaces. For example, some specific body areas have rather compressible tissue (the upper pectoral and calf area being some examples), and when positioned in these body areas, the device is configured to provide consistently good connectivity.

In one example, the filler applies a pressure greater than that for coupling the optics 1440 to the skin. This additional pressure decreases the transmural pressure as seen across the capillary walls which commensurately increases the elasticity of the capillaries which ultimately yields a larger PPG signal amplitude with improvements to signal to noise ratio.

In one example, device 1400 includes an ancillary sensor. The ancillary sensor can be a component of the electronics 1420, optics 1440, or other component. The ancillary sensor can include an accelerometer or a gyro sensor. An output signal from the ancillary sensor can be used for artifact correction. For example, the output signal can be used to cancel out motion artifacts. The output signal can be monitored in parallel or shortly before or after receiving the optical signals. In one example, the ancillary sensor signal can be configured to provide information for a calibration function (applied pressure, body position).

VARIOUS NOTES & EXAMPLES

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A device comprising:
   a sensor module including an optical sensor, the optical sensor including a light source and a light detector and configured to provide an electrical output on a node, the electrical output corresponding to a physiological parameter based on reflected light detected at a sensor surface; and
   a membrane having a contact side and having an opposing side, the contact side configured to conform to a tissue surface, the membrane having an engagement feature and the sensor module having a complementary feature configured to couple and decouple with the engagement feature, the engagement feature and the complementary feature configured to retain the sensor module in fixed alignment with the membrane; and
   wherein the sensor module includes an elastic filler disposed between the optical sensor and an electronic circuit, the optical sensor coupled to the electronic circuit by a conductor, the elastic filler configured to exert a compressive force on the optical sensor.

2. The device of claim 1 wherein the engagement feature includes an elastic element.

3. The device of claim 1 wherein the engagement feature includes a user-operable clip.

4. The device of claim 1 wherein the membrane includes a channel having a first port on the contact side and having a second port on the opposing side.

5. The device of claim 4 wherein the channel is configured to convey an adhesive solvent from the opposing side to the contact side.

6. The device of claim 1 wherein the membrane includes a porous substrate.

7. The device of claim 1 further including a solvent reservoir coupled to the membrane, the reservoir fluidly coupled to the contact side.

8. The device of claim 7 further including a barrier between the reservoir and the contact side.

9. The device of claim 8 wherein the barrier is user removable.

10. The device of claim 1 wherein the membrane has a slot.

11. The device of claim 1 wherein the membrane includes a notch configured to allow flexure of the membrane.

12. A device comprising:
    a sensor module including an optical sensor, the optical sensor including a light source and a light detector and configured to provide an electrical output on a node, the electrical output corresponding to a physiological parameter detected at a sensor surface; and
    a membrane having a contact side and having an opposing side, the contact side configured to conform to a tissue surface, the membrane having an aperture and having a pocket aligned with the aperture and configured to receive the sensor module, the pocket having fixed walls and the aperture configured to allow passage of the sensor module, the contact side configured to receive an adhesive coating; and
    wherein the sensor module includes an elastic filler coupled to the optical sensor and configured to exert a compressive force on the optical sensor.

13. The device of claim 12 wherein the membrane includes a plurality of pores.

14. The device of claim 13 wherein the pores are configured to convey a solvent for the adhesive coating.

15. The device of claim 12 wherein the membrane includes a non-woven material.

16. The device of claim 12 wherein the membrane includes at least one of a foam, an elastomer or a textile.

17. The device of claim 12 further including at least one support rib between the opposing side and the pocket.

* * * * *